US006593134B1

United States Patent

(12) United States Patent
Calnek et al.

(10) Patent No.: US 6,593,134 B1
(45) Date of Patent: Jul. 15, 2003

(54) METHOD OF PROPAGATING CHICKEN INFECTIOUS ANEMIA VIRUS

(75) Inventors: Bruce W. Calnek, Ithaca, NY (US); Benjamin Lucio-Martinez, Ithaca, NY (US); Carol Cardona, Davis, CA (US); Raymond W. Harris, Dryden, NY (US); Karel A. Schat, Ithaca, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

(21) Appl. No.: 09/522,761

(22) Filed: Mar. 10, 2000

(51) Int. Cl.$^{7}$ .......................... C12N 15/00; C12N 7/00; C12N 1/70

(52) U.S. Cl. ........................ 435/325; 435/5; 435/235.1; 435/236; 435/239

(58) Field of Search .............................. 435/325, 235.1, 435/236, 239, 5; 424/229.1

(56) References Cited

U.S. PATENT DOCUMENTS

| | | | |
|---|---|---|---|
| 5,491,073 | A | 2/1996 | Noteborn et al. |
| 5,554,525 | A | 9/1996 | Sondermeijer et al. |
| 5,686,077 | A | 11/1997 | Schrier |
| 5,728,569 | A | 3/1998 | Schrier |
| 5,789,567 | A | 8/1998 | Schat et al. |
| 5,914,113 | A | 6/1999 | Schrier |
| 5,965,139 | A | 10/1999 | Schat et al. |

OTHER PUBLICATIONS

Yusasa, "Propagation and Infectivity Titration of the Gifu–1 Strain of Chicken Anemia Agent in a Cell Line (MDCC–MSB1) Derived from Marek's Disease Lymphoma," *Natl. Inst. Anim. Health Q.* (*Jpn.*)23:13–20 (1983).*

Chandratilleke et al., "Characterization of Proteins Chicken Infectious Anemia Virus with Monoclonal Antibodies," *Avian Diseases* 35:854–862 (1991).

Renshaw et al., "A Hypervariable Region in VPI of Chicken Infectious Anemia Virus Mediates Rate of Spread and Cell Tropism in Tissue Culture," *Journal of Virology* 70:8872–8872 (1996).

Zhou et al., "Isolation and Identification of Chicken Infectious Anemia Virus in China," *Avian Diseases* 41:361–364 (1997).

Todd et al., "Effect of Multiple Cell Culture Passages on the Biological Behaviour of Chicken Anaemia Virus," *Avian Pathology* 27:74–79 (1998).

Lucio–Martinez et al., "Comparative Susceptibility of Avian Cell Lines to Chicken Infectious Anemia Virus," AVMA Annual Convention, p. 126 (1992) (abstract).

Schat et al., "Transformation of T–Lymphocyte Subsets by Marek's Disease Herpesvirus," *J. of Virology* 65:1408–1413 (1991).

Goryo et al., "Serial Propagation and Purification of Chicken Anaemia Agent in MDCC–MSB1 Cell Line," *Avian Pathology* 16:149–163 (1987).

Otaki et al., "Isolation of Chickens Anaemia Agent and Marek's Disease Virus From Chicken Vaccinated With Turkey Herpesvirus and Lesions Induced in Chicks by Inoculating Both Agents," *Avian Pathology* 16:291–306 (1987).

Lamichhane et al., "Pathogenicity of CL–1 Chicken Anemia Agent," *Avian Diseases* 35:515–522 (1991).

Calnek et al., "Pathogenesis of Marek's Disease Virus–Induced Local Lesions. 1. Lesion Characterization and Cell Line Establishment," *Avian Diseases* 33:291–302 (1989).

Calnek et al., "Pathogenesis of Marek's Disease Virus–Induced Local Lesions. 2. Influence of Virus Strain and Host Genotype," *Advances in Marek's Disease Research*, Proc. 3$^{rd}$ International Symposium on Marek's Disease, Osaka, Japan, pp. 324–330 (Sep. 12–16, 1988).

Goodwin et al., "Isolation and Identification of a Parvovirus–Like Virus (The So–Called Chick Anemia Agent [CAA]) That Causes Infectious Anemia in Chicks," Proc. 38$^{th}$ Western Poultry Disease Conf., Tempe, AZ, pp. 21–23 (1989).

Villegas et al., "Titration of Biological Suspensions," *Laboratory Manual for the Isolation and Identification of Avian Pathogens*, Third Edition, American Association of Avian Pathologists, pp. 186–190 (1989).

* cited by examiner

*Primary Examiner*—Ali R. Salimi
(74) *Attorney, Agent, or Firm*—Nixon Peabody LLP

(57) ABSTRACT

The present invention relates to a method of propagating chicken infectious anemia virus (CIAV). This method involves providing a Marek's disease chicken cell line—CU147 culture and inoculating the culture with a chicken infectious anemia virus under conditions effective to propagate the virus in the culture. The present invention also relates to methods of isolating, identifying, and quantifying chicken infectious anemia virus in a sample which includes providing a biological sample, providing a Marek's disease chicken cell line—CU147 culture, incubating the culture with the biological sample under conditions effective to allow a chicken infectious anemia virus to infect the culture, and isolating, identifying, or quantifying the virus in the culture. The present invention also relates to a high titer vaccine formulation for chicken infectious anemia virus which includes an immunologically effective amount of chicken infectious anemia virus propagated in a Marek's disease chicken cell line—CU147 culture. Another aspect of the present invention is a method of immunizing poultry against chicken infectious anemia virus which includes administering a vaccine prepared from chicken infectious anemia virus propagated in a Marek's disease chicken cell line—CU147 culture in an amount effective to induce an immune response to the virus.

4 Claims, No Drawings

METHOD OF PROPAGATING CHICKEN INFECTIOUS ANEMIA VIRUS

FIELD OF THE INVENTION

The present invention relates to methods for isolating, identifying, quantifying, and propagating chicken infectious anemia virus, in particular, for vaccine production.

BACKGROUND OF THE INVENTION

Chicken infectious anemia virus (CIAV), also known as chicken anemia virus (CAV) or chicken anemia agent (CAA), belongs to the group of Circoviridae. CIAV was first isolated in Japan in 1979 during an investigation of a Marek's disease vaccination break (Yuasa et al., *Avian Dis.* 23:366–385 (1979)). Since that time, CIAV has been detected in commercial poultry in all major poultry producing countries (von Bülow et al., in *Diseases of Poultry*, $10^{th}$ edition, Iowa State University Press, pp. 739–756 (1997)).

CIAV can cause clinical disease, characterized by anemia, hemorrhages and immunosuppression, in young susceptible chickens. Atrophy of the thymus and of the bone marrow are characteristic and consistent lesions of CIAV-infected chickens. Lymphocyte depletion in the thymus, and occasionally in the bursa of Fabricius, results in immunosuppression and increased susceptibility to secondary viral, bacterial, or fungal infections which then complicate the course of the disease. Infection of young chicks (less than 3 weeks) causes anemia, immunosuppression, morbidity and sometimes mortality if the chicks are free of maternal antibodies against CIAV. In chickens with maternal antibodies virus replication is suppressed until the antibodies disappear at approximately 3 weeks of age. After 3 weeks of age, infection is mostly subclinical but may cause changes in production of cytokines affecting the development of optimal immune responses to natural infections and vaccinations. The immunosuppression may cause aggravated disease after infection with one or more of Marek's disease virus (MDV), infectious bursal disease virus, reticuloendotheliosis virus, adenovirus, or reovirus. It has been reported that pathogenicity of MDV is enhanced by CIAV (deBoer et al., In *Proceedings of the* $38^{th}$ *Western Poultry Diseases Conference*, p. 28, Tempe, Ariz. (1989)). Further, it has been reported that CIAV aggravates the signs of infectious bursal disease (Rosenberger et al., *Avian Dis.* 33:707–713 (1989)). Additionally, subclinical CIAV infection in older chickens is correlated with decreased performance in broiler flocks (McNulty et al., *Avian Dis.* 35:263–268 (1991)). CIAV is highly resistant to environmental inactivation and some common disinfectants, characteristics that may potentiate disease transmission. The economic impact of CIAV infection on the poultry industry is reflected by mortality of 10% to 30% in disease outbreaks, a possible role in vaccine failures, and lower performance of infected flocks due to subclinical infection.

CIAV is a small, non-enveloped icosahedral virus of 25 nm diameter, and contains a genome consisting of 2.3 kb circular, single-stranded DNA. Two polypeptides have been detected in purified virus preparations; a major polypeptide of about 50 kilodaltons (kDa) termed VP1, and a 24 kDa polypeptide termed VP2. These two polypeptides together form a major epitope for the production of virus-neutralizing antibodies. Genomic DNA sequences of several different isolates of CIAV have been reported. Isolate Cux-1 was sequenced by Noteborn et al. (Noteborn et al., *J. Virol.* 65:3131–3139 (1991)) revealing 3 open reading frames (ORFs) that potentially encode polypeptides of 51.6 kDa, 24.0 kDa, and 13.6 kDa. As positioned in the genome, the three ORFs either partially or completely overlap one another. There was only one promoter-enhancer region upstream of the ORFs, and a single polyadenylation signal downstream of the ORFs. A single unspliced mRNA of 2100 bases is transcribed from the Cux-1 genome (Noteborn et al., *Gene* 118:267–271 (1992)). Another group also sequenced the Cux-1 strain; however, differences were noted between their sequence data and those from Noteborn et al. (Mechan et al., *Arch. Virol.* 124:301–319 (1992)). The nucleotide sequence of strain 26P4, isolated in the U.S.A., also showed a number of nucleotide differences when compared with sequences of Cux-1 (Claessens et al., *J. Gen. Virol.* 72:2003–2006 (1991)). Despite the differences in nucleotide sequences found in various isolates from around the world, only minor differences in amino acid sequences have been noted. For these reasons, it has been assumed that CIAV is a highly conserved virus.

Presently, the process by which CIAV causes chicken infectious anemia is poorly understood. When strain CIA-1 is introduced into susceptible 1-day old chicks, CIA-1 produces signs and lesions characteristic of chicken infectious anemia including low hematocrit values, depletion of erythrocytes and lymphoid cells in the bone marrow, depletion of lymphoid cells of the medulla and the cortex of the thymus (herein referred as T-cells), and inflammatory changes in the liver, heart and kidney (Lucio et al., *Avian Dis.* 34:146–153 (1990)). One or more of the polypeptides encoded by the CIAV ORFs may play a role in the pathogenesis of chicken infectious anemia by facilitating invasion into susceptible cells, and/or initiating T-cell apoptosis.

Exposing hens to CIAV may induce maternal antibody in chickens which may help protect against CIAV infections in their progeny. However, such vaccination with any of the CIAV strains has inherent problems including the potential of vertical (through the egg) transmission, and contamination of the environment. It is therefore desirable to develop a vaccine having as the immunogen a purified polypeptide(s) associated with CIAV.

When CIAV was first isolated in 1979, (Yuasa et al., "Isolation and Some Characteristics of an Agent Inducing Anemia in Chicks," *Avian Dis.* 23:366–385 (1979)), the only method of propagation was by chick inoculation. The Gifu strain of CIAV was subsequently found by Yuasa et al. (Yuasa, "Propagation and Infectivity Titration of the Gifu-1 Strain of Chicken Anemia Agent in a Cell Line (MDCC-MSB1) Derived From Marek's Disease Lymphoma," *Nat. Inst. Anim. Health Q.* 23:13–20 (1983)) to replicate in two lymphoblastoid cell lines, Marek's disease cell culture (MDCC)-MSB1 (MSB1) (Akiyama et al., "Two Cell Lines From Lymphomas of Marek's Disease," *Biken J.* 17:105–116 (1974)), and MDCC-JP2 (Yamaguchi et al., "Establishment of Marek's Disease Lymphoblastoid Cell Lines from Chickens with BABK of B Blood Groups," *Biken J.* 22:35–40 (1979)), and the lymphoblastoid avian leukosis virus-transformed cell line, LSCC-1104X5 (Hihara et al., "Establishment of Tumor Cell Lines Cultured From Chickens With Avian Lymphoid Leukosis," *Nat. Inst. Anim. Health Q.* 14:163–173 (1974)). Two other Marek's disease cell lines, MDCC-RP1 (Nazerian et al., "A Nonproducer T Lymphoblastoid Cell Line From Marek's Disease Transplantable Tumor (JMV)," *Avian Dis.* 21:69–76 (1977)) and MDCC-BP1 (Yuasa, "Propagation and Infectivity Titration of the Gifu-1 Strain of Chicken Anemia Agent in a Cell Line (MDCC-MSB1) Derived From Marek's Disease Lymphoma," *Nat. Inst. Anim. Health Q.* 23:13–20 (1983)), and one lymphoid leukosis line, LSCC-TLT-1 (current terminology: LSCC-CU 10) (Calnek et al., "Establishment of Marek's Disease Lymphoblastoid Cell Lines From Transplantable Versus Primary Lymphomas," *Int. J. Cancer* 21:100–197 (1978)) apparently failed to support the growth of the virus. More recent reports (Chandratilleke et al., "Characterization of Proteins of Chicken Infectious Anemia Virus with Monoclonal Antibodies," *Avian Dis.* 35:854–862 (1991) and Renshaw et al., "A Hypervariable Region in VP1 of Chicken Infectious Anemia Virus Mediates Rate of Spread and Cell Tropism in Tissue Culture," *J. Virology* 70:8872–8878 (1996)) suggest that other MD cell lines such as MDCC-CU22 (Calnek et al., "Spontaneous and Induced Herpesvirus Genome Expression in Marek's Disease Tumor Cell Lines," *Infect. Immun.* 34:483–491 (1981)) and a reticuloendotheliosis virus-transformed T-cell line, RECC-CU205 (Schat et al, "Stable Transfection of Reticuloendotheliosis Virus-Transformed Lymphoblastoid Cell Lines," *Avian Dis.* 36:432–439 (1992)), also are susceptible to one or more strains of CIAV. The virus also can be propagated in chicken embryos (von Bülow et al., "Chicken Vermehrung des Erregers der Aviären Infektiosen Anämie (CAA) in Embryonierten Hühnereiem," *J. Vet. Med.* B 33:664–669 (1986)).

MSB1 cells, characterized as mature helper T lymphocytes (CD3+, CD4+, CD8−, TCR2+) (Adair et al., "Characterization of Surface Markers Present on Cells Infected by Chicken Anemia Virus in Experimentally Infected Chickens," *Avian Dis.* 37:943–950 (1993)), are the most commonly reported substrate used for in vitro isolation, propagation, and titration of CIAV (von Bülow et al., "Chicken Infectious Anemia," *Diseases of Poultry*, $10^{th}$ ed., Iowa State University Press, pp. 739–756 (1997) and McNulty, "Chicken Anaemia Agent: a Review," *Avian Pathol.* 20:187–203 (1991)). Criteria of infection of MSB1 cultures include cytopathic effects and detection of viral antigen(s) by immunofluorescence (IF) tests or other methods. Although these cells appear to be the preferred substrate for in vitro infection with many strains of CIAV, some virus strains have been reported to not infect certain sublines of MSB1, or to do so only poorly. For instance, Cux-1 (von B ülow et al., "Frühsterblichkeitssyndrom bei Küken nach Doppelinfektion mit dem Virus der Marekshen Krankheit (MDV) und einem Anämi-Erreger (CAA)," *Veterinaermed Reihe* B 30:742–750 (1983)), CIA-1 (Lucio et al., "Identification of the Chicken Anemia Agent, Reproduction of the Disease, and Serological Survey in the United States," *Avian Dis.* 34:146–153 (1990)), and L-028 (Renshaw et al., "A Hypervariable Region in VP1 of Chicken Infectious Anemia Virus Mediates Rate of Spread and Cell Tropism in Tissue Culture," *J. Virology* 70:8872–8878 (1996)) all were found to replicate in one subline of MSB1, MSB1(S), but only Cux-1 replicated in a second subline, MSB1(L) and then to a lesser degree than in MSB12 (S). Furthermore, strain CIA-1 grew more slowly than Cux-1 in MSB12(S) cells. In a preliminary report by Lucio et al. in 1992 (Lucio-Martinez et al, "Comparative Susceptibility of Avian Cell Lines to Chicken Infectious Anemia Virus (abstract)," *Proc.* $129^{th}$ *Ann. Meet. Amer. Vet. Med. Assoc.* Boston, Mass. (1992)), there appeared to be substantial differences in CIAV-susceptibility among cell lines with some lines appearing to be more susceptible than MSB1(L) to the Cux-1 strain of CIAV.

The present invention is directed to overcoming the deficiencies in the prior art in isolating, identifying, quantifying, and propagating chicken infectious anemia virus.

SUMMARY OF THE INVENTION

The present invention relates to a method of propagating chicken infectious anemia virus. This method involves providing a Marek's disease chicken cell line—CU147 culture and inoculating the culture with a chicken infectious anemia virus under conditions effective to propagate the virus in the culture.

The present invention also relates to a method of isolating chicken infectious anemia virus from a sample. This method involves providing a biological sample infected with a chicken infectious anemia virus, providing a Marek's disease chicken cell line—CU147 culture, incubating the culture with the biological sample under conditions effective to allow the virus to infect the culture, and isolating the virus from the culture.

Another aspect of the present invention is a method for identifying chicken infectious anemia virus in a sample. This method involves providing a biological sample potentially containing a chicken infectious anemia virus, providing a Marek's disease chicken cell line—CU147 culture, incubating the culture with the biological sample under conditions effective to allow any of the virus present in the biological sample to infect the culture, and identifying the presence of any of the virus in the culture.

Yet another aspect of the present invention is a method for quantifying chicken infectious anemia virus in a sample. This method involves providing a biological sample containing a quantity of chicken infectious anemia virus, providing a Marek's disease chicken cell line—CU147 culture, incubating the culture with the biological sample under conditions effective to allow the virus to infect the culture, and titrating the quantity of virus in the culture.

The present invention also relates to a high titer vaccine formulation for chicken infectious anemia virus which includes an immunologically effective amount of chicken infectious anemia virus propagated in a Marek's disease chicken cell line—CU147 culture.

Another aspect of the present invention is a method of immunizing poultry against chicken infectious anemia virus which includes administering a vaccine prepared from chicken infectious anemia virus propagated in a Marek's disease chicken cell line—CU147 culture in an amount effective to induce an immune response to the virus.

The methods of the present invention can be used to replicate virus to higher titers than with prior art methods. In addition, the use of the methods of the present invention for the production of a vaccine results in improved yields of virus and, therefore, improved vaccine production. Moreover, the methods of the present invention can be used to produce high yields of virus and virus antigen to be used in diagnostic assays.

DETAILED DESCRIPTION OF THE INVENTION

The present invention relates to a method of propagating chicken infectious anemia virus (CIAV). This method involves providing a Marek's disease chicken cell line—CU147 (MDCC-CU147) culture (ATCC Accession No. PTA-1476) and inoculating the culture with a chicken infectious anemia virus under conditions effective to propagate the virus in the culture.

Suitable virus strains of CIAV include, but are not limited to, CIA-1 strain (GenBank Accession No. L14767, which is hereby incorporated by reference), Cux-1strain (GenBank Accession No. M55918, which is hereby incorporated by reference), Gifu strain (Yuasa, "Propagation and Infectivity Titration of the Gifu-1 Strain of Chicken Anemia Agent in a Cell Line (MDCC-MSB1) Derived From Marek's Disease Lymphoma," *Nat. Inst. Anim. Health Q.* 23:13–20 (1983), which is hereby incorporated by reference), TK-5803 strain (Goryo et al., "Serial Propagation and Purification of Chicken Anaemia Agent in MDCC-MSB1 Cell Line," *Avian Pathology* 16:149–163 (1987), which is hereby incorporated by reference), CAA82-2 strain (Otaki et al., "Isolation of Chicken Anaemia Agent and Marek's Disease Virus from Chickens Vaccinated with Turkey Herpesvirus and Lesions Induced in Chicks by Inoculating Both Agents," *Avian Pathology* 16:291–306 (1987), which is hereby incorporated by reference), L-028 strain (ORF1: GenBank Accession No. U69549, which is hereby incorporated by reference), Conn strain (ConnB: ORF1: GenBank Accession No. U69548, which is hereby incorporated by reference), GA strain (Goodwin et al., "Isolation and Identification of a Parvovirus-Like Virus (The So-Called Chick Anemia Agent (CAA)) that Causes Infectious Anemia in Chicks," *Proc. 38$^{th}$ Western Poultry Disease Conference*, Tempe, Ariz., pp. 21–23 (1989), which is hereby incorporated by reference), 26P4 strain (GenBank Accession No. I-1141, which is hereby incorporated by reference), SR43 strain (Zhou et al., "Isolation and Identification of Chicken Infectious Anemia Virus in China," *Avian Diseases* 41:361–364 (1997), which is hereby incorporated by reference), and CL-1 strain (Lamichhane et al., "Pathogenicity of CL-1 Chicken Anemia Agent," *Avian Diseases* 35:515–522 (1991), which is hereby incorporated by reference).

Cell lines such as the MDCC-CU147 cell line can be provided by numerous techniques known to those of ordinary skill in the art. In particular, the MDCC-CU147 cell line can be derived from Marek's disease lymphomas induced in chickens. Virus strains which can be used to induce tumors include: the low-oncogenicity strain CU-2 (Smith et al., "Effect of Virus Pathogenicity on Antibody Production in Marek's Disease," *Avian Dis.* 17:727–736 (1973), which is hereby incorporated by reference); moderate-oncogenicity strains BC-1 (Murthy et al., "Pathogenesis of Marek's Disease: Early Appearance of Marek's Disease Tumor-Associated Surface Antigen in Infected Chickens," *J. Natl. Cancer Inst.* 61:849–854 (1978), which is hereby incorporated by reference), ConnB (Jakowski et al., "Hematopoietic Destruction in Marek's Disease Viruses in Chickens," *Avian Dis.* 14:374–385 (1970), which is hereby incorporated by reference), and JM-10 (Calnek, "Influence of Age at Exposure on the Pathogenesis of Marek's Disease," *J. Natl. Cancer Inst.* 51:929–939 (1973), which is hereby incorporated by reference); high-oncogenicity strain GA-5 (Calnek, "Influence of Age at Exposure on the Pathogenesis of Marek's Disease," *J. Natl. Cancer Inst.* 51:929–939 (1973), which is hereby incorporated by reference); and the very high-oncogenicity strain RB-1B (Schat et al., "Influence of Oncogenicity of Marek's Disease Virus on Evaluation of Genetic Resistance," *Poult. Sci.* 60:2559–2566 (1981), which is hereby incorporated by reference).

Further, cell lines such as the MDCC-CU147 cell line can be established from early local lesions induced by Marek's disease virus and alloantigens as described in Calnek et al., "Pathogenesis of Marek's Disease Virus-Induced Local Lesions. 2. Influence of Virus Strain and Host Genotype," In: *Advances in Marek's Disease Research*, Kato et al., Eds., Gapanses Association on Marek's Disease, Osaka, Japan, pp. 324–330 (1988) and Calnek et al., "Pathogenesis of Marek's Disease Virus-Induced Local Lesions. 1. Lesion Characterization and Cell Line Establishment," *Avian Dis.* 33:291–302 (1989), which are hereby incorporated by reference.

The preparation and maintenance of cultures of the MDCC-CU147 cell line may be effected by techniques which are well known in the art. For example, cultures may be seeded at 250,000 cells/ml in plastic flasks or in 24-well plastic plates in an appropriate medium, such as LM Hahn medium or Leibovitz's L-1 5-McCoy's 5A medium (Calnek et al., "Spontaneous and Induced Herpesvirus Genome Expression in Marek's Disease Tumor Cell Lines," *Infect. Immun.* 34:483–491 (1981), which is hereby incorporated by reference), and then incubated, e.g., in a 5% $CO_2$ atmosphere at approximately 40–41° C.

In a preferred embodiment, inoculation is at a level from about 20 $\mu$L undiluted virus/ml culture to about 100 $\mu$L undiluted virus/ml culture.

In the method of the present invention, MDCC-CU147 can be used to replicate the CIAV to higher titers than in sublines of MSB-1 (see Tables 2, 3, and 4 in the Examples, below). These results could not be expected based on the phenotype of MDCC-CU147 because other cell lines with a similar phenotype (Tables 1 and 3) are much less susceptible to infection with and the replication of CIAV. In addition, the use of MDCC-CU147 instead of other cell lines (e.g., MSB-1) for the production of a CIAV vaccine results in improved yields of virus providing a competitive advantage to any company using MDCC-CU147 for vaccine production or other purposes. In particular, the use of MDCC-CU147 allows production of high yields of virus and virus antigen to be used in diagnostic assays.

The present invention also relates to a method of isolating chicken infectious anemia virus from a sample. This method involves providing a biological sample infected with a chicken infectious anemia virus, providing a Marek's disease chicken cell line—CU147 culture, incubating the culture with the biological sample under conditions effective to allow the virus to infect the culture, and isolating the virus from the culture.

Suitable biological samples include blood, mucosal scrapings, semen, tissue biopsy, embryonal tissues, secretions and excretions, and swabs of bodily fluids.

The virus may be isolated from the infected cells of the culture using methods known to those of ordinary skill in the art. In particular, virus can be isolated from infected cells by co-cultivation of infected cells with MDCC-CU147 culture cells, or from extracts of infected cells obtained by any of the typical methods for virus extraction, such as sonication, centrifugation, and freeze-thaw, or from secretions, excretions, or swabs of other bodily fluids.

Another aspect of the present invention is a method for identifying chicken infectious anemia virus in a sample. This method involves providing a biological sample potentially containing a chicken infectious anemia virus, providing a Marek's disease chicken cell line—CU147 culture, incubating the culture with the biological sample under conditions effective to allow any of the virus present in the biological sample to infect the culture, and identifying the presence of any of the virus in the culture.

Suitable methods for identifying the presence of the virus in the culture, i.e., demonstrating the presence of viral proteins in the culture, include immunofluorescence tests, which may use a monoclonal antibody against one of the viral proteins or polyclonal antibodies (von Bülow et al., in *Diseases of Poultry*, 10$^{th}$ edition, Iowa State University Press, pp. 739–756 (1997), which is hereby incorporated by reference), polymerase chain reaction (PCR) or nested PCR (Soiné et al., *Avian Diseases* 37:467–476 (1993), which is hereby incorporated by reference), ELISA (von Bülow et al., in *Diseases of Poultry*, 10$^{th}$ edition, Iowa State University Press, pp. 739–756 (1997), which is hereby incorporated by reference), virus neutralization, or any of the common histochemical methods of identifying specific viral proteins.

The method of identifying chicken infectious anemia virus in a sample of the present invention is particularly applicable to the development of diagnostic tests. In particular, once the presence of the virus in the culture is identified, the viral proteins may be extracted from the culture and used as a substrate for a diagnostic test, e.g., ELISA, immunofluorescence techniques, and PCR techniques.

Yet another aspect of the present invention is a method for quantifying chicken infectious anemia virus in a sample. This method involves providing a biological sample containing a quantity of chicken infectious anemia virus, providing a Marek's disease chicken cell line—CU147 culture, incubating the culture with the biological sample under conditions effective to replicate the virus in the culture, and titrating the quantity of the virus in the culture.

Titrating the quantity of the virus in the culture may be effected by techniques known in the art, as described in Villegas et al., "Titration of Biological Suspensions," In: *A Laboratory Manual for the Isolation and Identification of Avian Pathogens*, $3^{rd}$ Ed., Purchase et al., Eds., Kendall/Hunt Publishing Co., Dubuque, Iowa, pp. 186–190 (1989), which is hereby incorporated by reference.

The present invention also relates to a high titer vaccine formulation for chicken infectious anemia virus which includes an immunologically effective amount of chicken infectious anemia virus propagated in a Marek's disease chicken cell line—CU147 culture.

CIAV can be cultured in the MDCC-CU147 culture to a titer of at least $5\times10^7$ tissue culture infective doses—fifty percent ($TCID_{50}$).

One embodiment of the present invention is a live vaccine. Live attenuated vaccines may be produced by methods known in the art. For example, live attenuated vaccines may be produced by passaging and propagating the CIAV in an appropriate cell culture, e.g., the MDCC-CU147 culture, followed by subsequent propagation and passaging in embryonated eggs (see U.S. Pat. No. 5,728,569 to Schrier et al., which is hereby incorporated by reference). The vaccines of the present invention containing a live attenuated CIAV strain can be prepared and marketed in the form of a suspension or as a lyophilized product in a manner known per se.

Another embodiment of the present invention is an inactivated vaccine which includes one or more isolates of inactivated CIAV propagated in an MDCC-CU147 culture.

Inactivation of CIAV (to eliminate reproduction of the virus) for use in the vaccine of the present invention can be achieved, in general, by chemical or physical means (see U.S. Pat. No. 5,728,569 to Schrier et al., which is hereby incorporated by reference). Chemical inactivation can be effected by treating the virus with, for example, enzymes, formaldehyde, beta-propiolactone, ethylene-imine, or a derivative thereof. If necessary, the inactivating compound can be neutralized after inactivation is complete. For example, material inactivated with formaldehyde can be neutralized with thiosulfate. Physical inactivation can be effected by subjecting the virus to energy-rich radiation, e.g., UV light, X-radiation, or gamma-radiation. If desired, the pH can be brought back to a value of about 7 after treatment.

The vaccines of the present invention are administered in a dose sufficient to induce an immune response to the CIAV (see U.S. Pat. No. 5,728,569 to Schrier et al., which is hereby incorporated by reference).

The vaccines of the present invention can be administered orally, parenterally, subcutaneously, intravenously, intramuscularly, intraperitoneally, by intranasal instillation, by intracavitary or intravesical instillation, intraocularly, intraarterially, intralesionally, or by application to mucous membranes, such as, that of the nose, throat, and bronchial tubes. They can be administered alone or with pharmaceutically or physiologically acceptable carriers, excipients, or stabilizers, and can be in solid or liquid form such as, powders, solutions, suspensions, or emulsions.

The CIAV propagated in a Marek's disease chicken cell line—CU147 culture of the present invention may be administered in injectable dosages by solution or suspension of these materials in a physiologically acceptable diluent with a pharmaceutical carrier. Such carriers include sterile liquids, such as water and oils, with or without the addition of a surfactant and other pharmaceutically and physiologically acceptable carriers, including adjuvants, excipients, or stabilizers. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions.

For use as aerosols, the CIAV propagated in a Marek's disease chicken cell line—CU147 culture of the present invention in solution or suspension may be packaged in a pressurized aerosol container together with suitable propellants, for example, hydrocarbon propellants like propane, butane, or isobutane with conventional adjuvants. The materials of the present invention also may be administered in a non-pressurized form such as in a nebulizer or atomizer.

As described above, a stabilizer may be added to the vaccine composition. Suitable stabilizers include SPGA (Bavarnik et al., *J. Bacteriology*, 59:509–522 (1950), which is hereby incorporated by reference), carbohydrates (such as sorbitol, mannitol, starch, sucrose, dextran, or glucose), proteins (such as albumin or casein), or degradation products thereof, and buffers (such as alkali metal phosphates).

In addition, suitable adjuvants can also be added to the vaccine formulation. Suitable compounds with adjuvant activity include vitamin-E acetate oil-in-water emulsion, aluminum hydroxide, phosphate, or oxide, mineral oil (e.g., BAYOL® and MARCOL®), and saponins.

Emulsifiers, such as TWEEN® and SPAN®, may also be added to the vaccine formulation.

Vaccines according to the present invention may contain combinations of the CIAV propagated in an MDCC-CU147 culture and one or more unrelated avian viruses. Suitable unrelated avian viruses include Newcastle Disease virus ("NDV"), Infectious Bronchitis virus ("IBV") (ATCC Accession Nos. VR-21, VR-22, VR-817, and VR-841), Infectious Bursal Disease virus (IBVD) (ATCC Accession Nos. VR-478, VR-2041, and VR-2161), Marek's Disease virus ("MDV") (ATCC Accession Nos. VR-585, VR-624, VR-987, VR-2001, VR-2002, VR-2103, VR-2175, VR-2176, and VR-2260), Herpes virus of Turkeys ("HVT") (ATCC Accession No. VR-584B), Infectious Laryngotracheitis virus (ATCC Accession No. VR-783) or other avian herpes, Reo virus, Egg Drop Syndrome virus, Avian Encephalomyelitis virus (ATCC Accession Nos. VR-713 and VR-2058), Reticuloendotheliosis virus (ATCC Accession Nos. VR-770, VR-994, 45011, 45012, 45013, and 45158), Leukosis virus (ATCC Accession Nos. VR-247, VR-335, VR-658, and VR-773), Fowlpox virus (ATCC Accession Nos. VR-229, VR-249, VR-250, and VR-251), Turkey Rhinotracheitis virus ("TRTV"), Adenovirus, or Avian Influenza virus (ATCC Accession No. VR-40).

Another aspect of the present invention is a method of immunizing poultry against chicken infectious anemia virus which includes administering a vaccine prepared from chicken infectious anemia virus propagated in a Marek's disease chicken cell line—CU147 culture in an amount effective to induce an immune response to the virus.

This method includes the administration of live or inactivated vaccines.

EXAMPLES

Example 1

Preparation of Cell Lines

MSB1(S) and MSB1(L) have been described (Renshaw et al., "A Hypervariable Region in VP1 of Chicken Infectious Anemia Virus Mediates Rate of Spread and Cell Tropism in Tissue Culture," *J. Virology* 70:8872–8878 (1996), which is hereby incorporated by reference). Briefly, the "S" subline (unknown passage level) was obtained from G. Thiry, Solvay Animal Health, Mendota Heights, Minn., whereas the "L" subline was received as passage-96 from R. L. Witter, USDA Animal Disease and Oncology Laboratory, E. Lansing, Mich. MSB1(S) cultures which were used had been maintained in the laboratory for approximately 26 to 58 days in culture (DIC) after receipt (X+26 DIC to X+58 DIC). MSB1(L) cells were used as $122^{nd}$ to $367^{th}$ passage cultures.

MDCC-CU12, -CU14, -CU32, and -CU36 (Calnek et al, "Spontaneous and Induced Herpesvirus Genome Expression in Marek's Disease Tumor Cell Lines," *Infect. Immun.* 34:483–491 (1981), which is hereby incorporated by reference) were derived from Marek's disease (MD) lymphomas and were used after 90, 150, 115, and 115 DIC, respectively. All other cell lines were established from early local lesions induced by Marek's disease virus (MDV) and alloantigens (Calnek et al, "Pathogenesis of Marek's Disease Virus-Induced Local Lesions. 1. Lesion Characterization and Cell Line Establishment," *Avian Dis.* 33:291–302 (1989) and Schat et al., "Transformation of T-Lymphocyte Subsets by Marek's Disease Herpesvirus," *J. Virology* 65:1408–1413 (1991), which are hereby incorporated by reference). These lines were all of the same genotype, i.e., from S-13 chickens ($B^{13}\ B^{13}$) (Schat et al, "Cultivation and Characterization of Avian Lymphocytes with Natural Killer Cell Activity," *Avian Pathol.* 15:539–556 (1986), which is hereby incorporated by reference), and infected with the GA-5 strain of MDV (Calnek, "Influence of Age at Exposure on the Pathogenesis of Marek's Disease," *J. Nat. Cancer Inst.* 51:929–939 (1973), which is hereby incorporated by reference). They were used after 21 to 131 DIC. All cell lines and surface-marker characteristics are listed in Table 1, below.

TABLE 1

Phenotypic characterization of cell lines.[A]

| CD4+/CD8− | | CD4−/CD8+ | | CD4−/CD8− | |
|---|---|---|---|---|---|
| TCR2+ | TCR3+ | TCR2+ | TCR3+ | TCR2+ | TCR3+ |
| MSB1 (S) | CU12 | CU88 | CU82 | CU86 | CU108 |
| MSB1 (L) | CU14[B] | CU94 | CU105 | CU109[C] | CU123 |
| CU32 | | CU139 | CU112 | CU133 | |

TABLE 1-continued

Phenotypic characterization of cell lines.[A]

| CD4+/CD8− | | CD4−/CD8+ | | CD4−/CD8− | |
|---|---|---|---|---|---|
| TCR2+ | TCR3+ | TCR2+ | TCR3+ | TCR2+ | TCR3+ |
| CU36 | | CU145[D] | CU147 | CU140 | |
| CU78 | | CU150 | | CU151 | |
| CU95 | | | | | |
| CU137 | | | | | |
| CU141 | | | | | |

[A]Classification based on indirect immunofluorescence tests with monoclonal antibodies.
[B]Previously classified as CD4+/CD8−, TCR2 (Schat et al., "Transformation of T-lymphocyte Subsets by Marek's Disease Herpesvirus," *J. Virology* 65:1408–1413 (1991), which is hereby incorporated by reference)
[C]Previously classified at CD4−/CD8+, TCR3 (Schat et al., "Transformation of T-lymphocyte Subsets by Marek's Disease Herpesvirus," *J. Virology* 65:1408–1413 (1991), which is hereby incorporated by reference)
[D]Previously classified at CD4−/CD8−, TCR2 (Schat et al., "Transformation of T-lymphocyte Subsets by Marek's Disease Herpesvirus," *J. Virology* 65:1408–1413 (1991), which is hereby incorporated by reference)

To determine surface markers, all cell lines were subjected to IF tests using methods and monoclonal antibodies as described in Schat et al., "Transformation of T-lymphocyte Subsets by Marek's Disease Herpesvirus," *J. Virology* 65:1408–1413 (1991), which is hereby incorporated by reference.

Example 2

Culture Inoculation and Maintenance

Cultures were seeded at 250,000 cells/ml in 25 $cm^2$ plastic flasks or in 24-well plastic plates in LM Hahn medium (Calnek et al., "Spontaneous and Induced Herpesvirus Genome Expression in Marek's Disease Tumor Cell Lines," *Infect. Immun.* 34:483–491 (1981), which is hereby incorporated by reference) modified by reducing the chicken serum to 4% and incubated in a 5% $CO_2$ atmosphere at 41° C. The chicken serum used in the medium was collected from specific-pathogen-free chickens known to be free of CIAV infection and confirmed to be CIAV-free by PCR, as described below. Inoculations with virus were at the rate of 100 μL/ml (Experiment 1) or 20 μL/ml (all others). Cultures were split by adding additional medium every 2–3 days, generally at the time of sampling.

Example 3

Virus Strains, Titrations

The origins of two virus strains, Cux-1 (von Bülow et al., "Frühsterblichkeitssyndrom bei Küken nach Doppelinfektion mit dem Virus der Marekshen Krankheit (MDV) und einem Anämi-Erreger (CAA)," *Veterinaermed* Reihe B 30:742–750 (1983), which is hereby incorporated by reference) and CIA-1 (Lucio et al., "Identification of the Chicken Anemia Agent, Reproduction of the Disease, and Serological Survey in the United States," *Avian Dis.* 34:146–153 (1990), which is hereby incorporated by reference), have been described (Renshaw et al., "A Hypervariable Region in VP1 of Chicken Infectious Anemia Virus Mediates Rate of Spread and Cell Tropism in Tissue Culture," *J. Virology* 70:8872–8878 (1996), which is hereby incorporated by reference)). For these studies, two batches of Cux-1 strain were used. Batch 1 had a total of 6 passages in MSB1 (L) cells following its receipt. Batch 2 was passaged 3 times in MSB1 (L) cells and once in MSB1 (S)

cells prior to a final passage in CU147 cells. CIA-1 was used as bird-propagated virus in the form of an infected liver extract ($3.9\times10^4$ chicken minimal infective doses/ml) (Batch 1) or after 2 subsequent passages in CU147 cells (Batch 2).

For titrations, samples of inoculated cultures were examined by the IF test and the titer was based on the presence or absence of infection. Minimal infective dose (MID) endpoints were determined as the last dilution to be positive when only one culture was inoculated per dilution. In titrations with 4 cultures per dilution, endpoints were calculated by the method of Reed and Muench (Reed et al., "A Simple Method for Estimating Fifty Percent Endpoints," *Amer. J. Hygiene* 27:493–497 (1938), which is hereby incorporated by reference). The titer of Batch-1 was approximately 10 MID/ml in MSB1 (L) cells whereas that of Batch-3 was determined to be $5.0\times10^5$ tissue culture infective doses-50% ($TCID_{50}$)/ml in MSB1 (S) cells. The tissue culture-propagated CIA-I virus, Batch 2, had a titer of $6.9\times10^6$ $TCID_{50}$/ml in MSB1 (S) cells.

Example 4

Immunofluorescence Tests for Viral Antigen

Monoclonal antibody 51.3, specific for CIAV viral protein 3 (Chandratilleke et al., "Characterization of Proteins of Chicken Infectious Anemia Virus with Monoclonal Antibodies," *Avian Dis.* 35:854–862 (1991), which is hereby incorporated by reference), was applied to air-dried, acetone-fixed smears of 50,000 cells on 12-well slides. After 15 minutes of incubation in a moist 37° C. chamber, the slides were washed in phosphate-buffered saline (PBS), and then stained with goat anti-mouse antibodies conjugated with fluorescein isothiocyanate for another 15 minutes in the moist chamber. Coverslips were applied after another PBS wash and the smears were examined using a fluorescence microscope with epi-illumination. Positive cells were counted by examination of the entire smear, or the number was estimated by counting a known portion of the smear in moderately infected cultures, or was determined by estimating the percentage of infected cells in heavily infected cultures. The rate of infection is reported as the number of positive cells per 50,000.

Example 5

DNA Extraction

DNA was extracted from each tissue culture sample using standard techniques (Moore, "Preparation and Analysis of DNA," *Current Protocols in Molecular Biology*, Vol. 1, Greene Publishing Associates and Wiley-Interscience, John Wiley and Sons, Inc., New York, N.Y. (1988), which is hereby incorporated by reference) with some modifications. Briefly, 1–2 ml of cells growing in suspension were pelleted and resuspended in 0.5 ml of the culture supernatant. The samples were then incubated overnight at 37–41° C. in digestion buffer (100 mM Tris-HCl, pH 8.0, 10 mM NaCl, 0.5% sodium dodecyl sulfate, and 0.2 $\mu$g/ml proteinase K). Each sample was extracted with a mixture of phenol:chloroform:isoamyl alcohol (25:24:1) once and the DNA precipitated at −20° C. with one volume of isopropyl alcohol and one-tenth volume 3 M NaCl overnight. The DNA was pelleted by centrifugation at 14,000×g, 4° C. for 20 minutes. The DNA was washed with 70% ethanol, resuspended in Tris-EDTA pH 7.4, and quantitated using a TD-360 fluorometer (Turner Designs, Inc., Sunnyvale, Calif.).

Example 6

Polymerase Chain Reaction (PCR)

For CIAV screening, a standard PCR method was used. The first reaction contained 100 ng of total DNA, 1.5 mM $MgCl_2$, 0.25 units Taq DNA polymerase (Gibco-BRL, Life Technologies, Gaithersburg, Md.), 1×PCR buffer (Gibco-BRL), 50 pmole each primer (primer O3F: CAAGTAATTTCAAATGAACG (SEQ. ID. No. 1), primer O3R: TTGCCATCTTACAGTCTTAT (SEQ. ID. No. 2)), and 0.25 mM each nucleotide triphosphate (NTP) in a 50 $\mu$L total volume. The reaction was performed for 35 cycles after a 5 minute denaturation at 94° C. (each cycle was 94° C. for 1 minute, 45° C. for 2 minutes, and 72° C. for 1 minute) followed by one extension step of 72° C. for 10 minutes.

One tenth of the volume of each PCR reaction was electrophoresed on a 1.5% agarose gel, stained with ethidium bromide, and visualized with ultraviolet light.

Example 7

Sequencing

Primers to CIA-1 were used to amplify a 461-bp fragment from the hypervariable region of VP-1, as identified by Renshaw et al., "A Hypervariable Region in VP1 of Chicken Infectious Anemia Virus Mediates Rate of Spread and Cell Tropism in Tissue Culture," *J. Virology* 70:8872–8878 (1996), which is hereby incorporated by reference. The PCR reaction mixture contained 100 ng of DNA, 1.5 mM $MgCl_2$, 0.25 units Taq DNA polymerase, 1×PCR buffer, 50 pmole each primer (primer O1F: AGGTGTATAAGACTGTAAG (SEQ. ID. No. 3), primer PshA1R: GAACAGGTGCCAGCCCCCAAACAT (SEQ. ID. No. 4)), and 0.25 mM each NTP in a 50 $\mu$L total volume. The PCR reaction was performed for 35 cycles after an initial 5 minute denaturation step at 94° C. (each cycle was 94° C. for 1 minute, 45° C. for 2 minutes, and 72° C. for 1 minute) followed by one extension step of 72° C. for 10 minutes. The PCR reactions were electrophoresed on a 1.5% agarose gel, the bands were removed, and DNA extracted with the Concert gel extraction kit (Gibco-BRL, Life Technologies, Gaithersburg, Md.) according to the manufacturer's instructions. DNA sequencing was done at the BioResource Center at Cornell University on Perkin Elmer Biosystems model 377-XL DNA sequencer (The Perkin-Elmer Corporation, Norwalk, Conn.) using dye-terminator chemistry.

Example 8

Sequence Analysis

Sequences were aligned with published CIAV sequences using the Clustal method of MegAlign (Windows 32 3.18 DNASTAR) software (DNASTAR, Inc., Madison, Wis.). GenBank accession numbers of the sequences used in the alignment are as follows: Cux-1 is M55918 and CIA-1 is L14767.

Example 9

Experimental Design

Two experiments were performed to compare the relative susceptibility of various cell lines representing three groups, CD4+/8−, CD4−/8+, and CD4−/8−. Two trials comprised Experiment 1 in which cell lines were inoculated with Batch-1 Cux-1 virus at the rate of 0.1 ml undiluted virus/1-ml culture (1 MID/culture). Cultures were examined at 4, 7, 10, and 17 days post inoculation (DPI) in trial 1 and at 3 and 7 DPI in trial 2. Five trials were conducted in Experiment 2 using Batch-2 Cux-1 inoculated at the rate of 20 $\mu$L of $10^{-3}$ virus dilution (approximately 10 $TICD_{50}$)/ml of culture. Examinations were at 2- to 3-day intervals from 3 to 9 or 10 DPI.

Comparative titrations of Cux-1 (Batch 2) and CIA-1 (Batch 2) were carried out using MSB1 (L), MSB1 (S), and CU147 cells in the course of 2 trials (Experiment 3). Samples from several of the individual cultures were screened for CIAV with PCR at the termination of the experiment.

Example 10

Phenotypic Characteristics of Cell Lines

Phenotypic classification of all cell lines tested is shown in Table 1. Discrepancies from previously reported phenotype classification (Schat et al., "Transformation of T-Lymphocyte Subsets by Marek's Disease Herpesvirus," *J. Virology* 65:1408–1413 (1991), which is hereby incorporated by reference) involved three lines: CU 14, CU 109, and CU 145 (see footnote, Table 1).

Example 11

Comparative Susceptibility of Cell Lines to Cux-1 CIAV (Experiments 1 and 2)

Results from Experiment 1, reported in Table 2, show clear-cut differences among lines in susceptibility to the Cux-1 strain of CIAV.

TABLE 2

Relative susceptibility of MDCC lines to the Cux-1 strain of chicken infectious anemia virus (Experiment 1).[A]

| Phenotype | Cell line - passage or days in culture (DIC) | Immunofluorescence tests: positive cells/50,000 3–4 DPI[B] | 7 DPI | 10 DPI |
|---|---|---|---|---|
| CD4+/8− | MSB1 (L) - 122 p | 0 | 0 | 0[C] |
| | MSB1 (L) - 131 p | 0 | 0 | —[D] |
| | CU12 - 90 DIC | 0 | 36 | 810 |
| | CU14 - 150 DIC | 0 | 0 | — |
| | CU32 - 115 DIC | 0 | 0 | — |
| | CU36 - 115 DIC | 0 | 14 | 1,618 |
| CD4−/8+ | CU94 - 47 DIC | 280 | 29,500 | — |
| | CU105 - 21 DIC | 286 | 10,700 | — |
| | CU105 - 39 DIC | 4 | 9,250 | — |
| | CU147 100 DIC | 792 | 30,056 | — |
| CD4−/8− | CU86 - 35 DIC | 0 | 1,166 | 10,100 |
| | CU108 - 66 DIC | 27 | 130 | 10,400 |
| | CU109 - 37 DIC | 106 | 12,950 | — |
| | CU109 - 55 DIC | — | 692 | — |
| | CU123 - 104 DIC | 2 | 2,426 | — |
| | CU133 - 125 DIC | 0 | 294 | — |

[A]One-ml cultures of 250,000 cells were inoculated with 100 $\mu$L of undiluted Batch-1 Cux-1 CIAV (estimated to be 1 minimal infective dose). All uninoculated controls negative at 7-DPI.
[B]DPI= days post inoculation
[C]This culture was still negative at 17 DPI
[D]—= not done Of the five CD4+/8− lines tested, only two, CU12 and CU36, showed signs of infection during the experimental period of 7 to 17 days. In contrast, all three CD4−/8+ and all five CD4−/8− lines had antigen-positive cells by 7 DPI. In one of the trials, MSB1 (L) cells were still negative after 17 days, suggesting that the culture truly failed to become infected. It should be noted that the titer of the inoculum for this experiment was very low (only I MID per culture), so the absence of infection in some lines should be viewed with caution and not necessarily taken to mean that the cultures were refractory to infection.

In Experiment 2 (Table 3), the dose of Cux-1 virus was somewhat higher (approximately 10 $TCID_{50}$/culture).

TABLE 3

Relative susceptibility of MDCC lines to the Cux-1 strain of chicken infectious anemia virus (Experiment 2).[A]

| Phenotype | Cell line - passage or Days in culture (DIC)[B] | Immunofluorescence tests: positive cells/50,000 3 DPI[C] | 5 DPI | 7 DPI | 10 DPI |
|---|---|---|---|---|---|
| CD4+/8− | MSB1 (L) - 150 p | 0 | 0 | —[D] | — |
| | MSB1 (L) - 367 p | 0 | 0 | 0 | 0 |
| | MSB1 (S) - X + 26 DIC | 0 | 52 | 325 | 27,500 |
| | MSB1 (S) - X + 33 DIC | 0 | 12 | 502 | — |
| | MSB1 (S) - X + 43 DIC | 0 | 8 | — | — |
| | MSB1 (S) - X + 51 DIC | 0 | 8 | — | — |
| | CU78 - 58 DIC | 0 | 20 | 276 | — |
| | CU95 - 75 DIC | 0 | 260 | 2,176 | — |
| | CU95 - 85 DIC | 0 | 138 | — | — |
| | CU137 - 61 DIC | 0 | 95 | 6,400 | — |
| CD4−/8+ | CU82 - 26 DIC | 1 | 57 | — | — |
| | CU88 - 30 DIC | 11 | 1,536 | — | — |
| | CU94 - 37 DIC | 25 | 6,400 | — | — |
| | CU112 - 79 DIC | 0 | 4 | | |
| | CU139 - 43 DIC | 0 | 86 | 2,400 | — |
| | CU145 - 43 DIC | 0 | 212 | 8,000 | — |
| | CU147 - 66 DIC | 88 | 30,000 | — | — |
| | CU147 - 94 DIC | 54 | 35,000 | — | — |
| | CU147 - 106 DIC | 105 | 35,000 | — | — |
| | CU147 - 116 DIC | 143 | 30,000 | — | — |
| | CU147 - 66 DIC | 88 | 30,000 | — | — |
| | CU147 - 94 DIC | 54 | 35,000 | — | — |
| | CU147 - 106 DIC | 105 | 35,000 | — | — |
| | CU147 - 116 DIC | 143 | 30,000 | — | — |
| | CU147 - 124 DIC | 1,664 | 47,000 | — | — |
| | CU150 - 47 DIC | 0 | 19 | — | — |
| CD4−/8− | CU109 - 57 DIC | 2 | 36 | | — |
| | CU140 - 45 DIC | 0 | 360 | 3,700 | — |
| | CU151 - 73 DIC | 0 | 251 | 3,200 | — |

[A]One-ml cultures of 280,000 cells were inoculated with 20 $\mu$L of $10^{-3}$ Batch-2 Cux-I CIAV. All uninoculated control cultures were negative at 5 DPI.
[B]Days in culture for MSBI(S) unknown. X = initial passage level (as obtained for these studies); subsequent days in culture are indicated as +26, for example.
[C]DPI= days post inoculation
[D]—=not done In this case, 4 of 8 CD4−/8+ lines and 1 of 3 CD4−/8− lines showed evidence of infection by 3 DPI, compared to none of 6 CD4+/8− lines. With the exception of MSB1(L), all lines were positive by 5 DPI, and all showed increases in the proportion of positive cells in sequential samplings. Five replicates of CU147 cells, 4 replicates of MSB1 (S), and 2 replicates each for MSB1 (L) and CU95 cells were included in the five trials comprising Experiment 2. The results from trial to trial with these lines were remarkably similar.

Example 11

Comparative Susceptibility of MSB1 and CU147 Cell Lines to Cux-1 and CIA-1 Strains of CIAV The initial attempt to adapt CIA-1 virus to cell culture was carried out in MSB1 (S) and CU147 cells inoculated in parallel with Batch-1 virus (liver extract). No evidence of infection was seen in periodic examinations until 9 DPI when the CU147 culture had a few (3/50,000) positive cells in IF tests. By 13 DPI, the infection rate had increased to 896/50,000 cells positive and at 17 DPI it had doubled to 1,920/50,000. The parallel culture of MSB1 (S) cells remained negative through 27 DPI. Undiluted virus harvested as supernatant fluid from the infected CU147 cells at 15 DPI was inoculated (0.5 ml per culture) into MSB1 (S) cells and CU147 cells for a second passage. At 2 DPI, infection was evident in the CU147 cells (60/50,000 positive) but not MSB1 (S) cells; by 4 DPI, the MSB1 culture had 4 positive cells/50,000 and the infection in the CU147 cells had increased to 7,168 positive. Virus harvested from the CU147 cells at 5 DPI constituted the Batch-2 stock of CIA-1 virus used in other experiments.

The relative susceptibility of MSB1 (S) and CU147 was further investigated by doing parallel titrations of Cux-1 and CIA-1 in both cell types. Results are found in Table 4.

dilution, and CIA-1 in MSB1 cells at the $10^{-5}$ dilution), one or two of the four replicates were positive by PCR but negative by IF. Of the cultures tested again at 10 DPI, only one (a replicate of $10^{-4}$ Cux-1 in MSB1 cells) changed its status from negative to positive in the IF test.

Four samples from the Cux-1 titrations ($10^{-3}$ and $10^{-4}$ in MSB1 cells and $10^{-5}$ and $10^{-6}$ in CU147 cells) and three samples from CIA-1 titrations ($10^{-3}$ and $10^{-5}$ in MSB1 cells and $10^{-5}$ in CU147 cells) were amplified and sequenced. In each case, the sequences of these samples matched those of the respective inocula (Cux-1 or CIA-1) in all positions where the two strains differ from each other.

TABLE 4

Titration of Cux-1 (Batch 2) and CIA-I (Batch 2) strains of CIAV in MSB1 (S) and CU147 cells. (Experiment 3)[A]

| | | Immunofluorescence tests: positive cells/50,000[B] | | | | | | | |
|---|---|---|---|---|---|---|---|---|---|
| | | MSB1 cells | | | | CU147 cells | | | |
| Virus | Dilution | 3 DPI | 6 DPI | 8 DPI | 10 DPI | 3 DPI | 6 DPI | 8 DPI | 10 DPI |
| Cux-1 | $10^{-3}$ | 0 | 34 | 119<br>7 | — | 72 | 30,000 | —[C] | — |
| | $10^{-4}$ | 0 | 5 | 47<br>(2/4) [2/4] | 28,000<br>(3/4) | 6 | 23,000 | — | — |
| | $10^{-5}$ | 0 | 0 | 0<br>(0/4) [0/4] | 0<br>(0/4) | 0 | 4,930 | >40,000<br>(4/4) [3/3] | — |
| | $10^{-5}$ | 0 | 0 | 0<br>(0/4) [0/4] | 0<br>(0/4) | 0 | 0 | 1,600<br>(1/4) [2/4] | 10,000<br>(1/4) |
| CIA-1 | $10^{-3}$ | 3 | 38 | 360<br>(4/4) [4/4] | — | 405 | >40,000 | — | — |
| | $10^{-4}$ | 0 | 1 | 39<br>(4/4) [2/2] | — | 38 | >40,000 | — | — |
| | $10^{-5}$ | 0 | 0 | 3<br>(2/4) [3/4] | — | 4 | 20,000 | — | — |
| | $10^{-6}$ | 0 | 0 | 0<br>(0/4) [0/4] | — | 0 | 4,030 | — | — |
| | $10^{-7}$ | — | 0 | — | — | — | 0 | — | — |

[A]Each virus dilution inoculated into 4 replicate cultures (single cultures for $10^{-7}$ dilution) at the rate of 20 μL/250,000 cells in 1 ml.
[B]A portion of each replicate pooled for examination at 3 and 6 days post inoculation (DPI). At 8 DPI. all replicates were examined individually. Data indicate the mean from the four samples. Figures in parentheses = number of replicates positive/number examined by IF test. Figures in brackets = numbers of replicates positive/number examined by PCR.
[C]— = not done.

It can be seen that the endpoint titers were higher, and the rate of virus spread (based on the number of virus-positive cells) was substantially higher for both virus strains in CU147 cells than in MSB1 (S) cells. The $TCID_{50}$ titers (calculated from 8-DPI examinations) for Cux-1 virus in MSB1 (S) cells and CU147 cells were $10^{5.7}$ and $10^{-7.4}$/ml, respectively. With CIA-1 virus, the 8-DPI $TCID_{50}$ titer was $10^{-6.7}$. Unfortunately, the titer in CU147 cells was not determined at 8 DPI; however, the MID titer of the CIA-1 virus strain at 6 DPI was at least 10 times higher in CU147 cells than in MSB1 cells. Also, it should be noted that the rate of spread of infection in the CU147 cells appeared to be very rapid, involving the majority of the cells within 6 to 8 days, even with low doses of virus.

Example 12

DNA Sequence Comparisons with Cux-1 and CIA-1 Strains of CIAV

PCR screening of the titration-endpoint cultures at 8 DPI confirmed the fluorescent antibody findings with a few exceptions. In three instances (see Table 4: Cux-1 in MSB1 cells at the $10^{-4}$ dilution, Cux-1 in CU-147 cells at the $10^{-6}$

Example 13

Comparative Susceptibility of Marek's Disease (MD) Cell Lines to CIAV

This was the first extensive comparison of various MD cell lines to determine their relative susceptibility to CIAV. Earlier studies by Yuasa (Yuasa, "Propagation and Infectivity Titration of the Gifu-1 Strain of Chicken Anemia Agent in a Cell Line (MDCC-MSB1) Derived From Marek's Disease Lymphoma," *Nat. Inst. Anim. Health Q.* 23:13–20 (1983), which is hereby incorporated by reference), Chandratilleke et al. (Chandratilleke et al., "Characterization of Proteins of Chicken Infectious Anemia Virus with Monoclonal Antibodies," *Avian Dis.* 35:854–862 (1991), which is hereby incorporated by reference), and Renshaw et al. (Renshaw et al., "A Hypervariable Region in VP1 of Chicken Infectious Anemia Virus Mediates Rate of Spread and Cell Tropism in Tissue Culture," *J. Virology* 70:8872–8878 (1996), which is hereby incorporated by reference) examined several virus strains but only a small number of cell lines, most of which were either known, or presumed to be, CD4+/8−, TCR2+, or 3+. Differences in susceptibility associated with either the cell line or the virus strain were reported. In the present study, lines of various phenotypes were included, such as CD4−/8+ and CD4−/8− lines in addition to the more usual CD4+/8− lines. This was possible because lines derived from MD local lesions (Calnek et al., "Pathogenesis of Marek's Disease Virus-Induced Local Lesions. 1. Lesion Characterization and Cell Line Establishment," *Avian Dis*. 33:291–302 (1989), which is hereby incorporated by reference) have a richly diverse group of phenotypes (Schat et al., "Transformation of T-lymphocyte Subsets by Marek's Disease Herpesvirus," *J. Virology* 65:1408–1413 (1991), which is hereby incorporated by reference). All of the latter, which made up the majority of the cell lines tested, were identical in terms of their genotype and the strain of transforming MDV. Thus it was possible to compare lines for differences based on phenotype alone.

It is clear from the data in Tables 2 and 3 that although there are differences in susceptibility to Cux-1 virus among the lines in the various phenotypes, the variability within phenotypes makes it difficult to draw conclusions regarding the effect of the phenotype itself. Although the most susceptible lines were either CD4−/8+ or CD4−/8−, several lines within these groups were no more susceptible than CD4+/8− lines. There was no apparent difference in susceptibility between TCR2+ and TCR3+ lines. One line, CU147, was strikingly consistent in being highly susceptible to Cux-1 virus. For that reason comparative tests with both Cux-1 and CIA-1 viruses were carried out in both MSB1 (S) and CU147 cells. Data in Table 4 illustrate the superiority of the latter for detecting either strain of CIAV in terms of the initial appearance of infected cells in IF tests, the speed of spread to involve a majority of the cells in a given culture, and the titer of virus detected within a 10-day culture period.

The difference in susceptibility between the two sublines of MSB1 was consistent with results reported by Renshaw et al., "A Hypervariable Region in VP1 of Chicken Infectious Anemia Virus Mediates Rate of Spread and Cell Tropism in Tissue Culture," *J. Virology* 70:8872–8878 (1996), which is hereby incorporated by reference. Although Data in Tables 3 and 4 suggest that the MSB1 (L) cells were refractory to infection by Cux-1 virus, this may be a reflection of the low titer of the inoculum and/or the short observation period in some of those trials. Other trials, carried out for longer periods or with more virus, confirmed that the line is susceptible, albeit only poorly so.

A major discrepancy between results reported by Renshaw et al., "A Hypervariable Region in VP1 of Chicken Infectious Anemia Virus Mediates Rate of Spread and Cell Tropism in Tissue Culture," *J. Virology* 70:8872–8878 (1996), which is hereby incorporated by reference, and those obtained in the Examples above has to do with the ability of CIA-1 virus to grow in CU147 cells. Renshaw et al. stated that repeated attempts to propagate CIA-1 in CU147 cells failed. Yet, in the Examples above the line was found to be very highly susceptible, even more so than MSB1 cells (this could be explained by the fact that the authors of the earlier study may have had some technical difficulties in growing the CU147 cell line). Also, it should be noted that the CIA-1 virus grew slowly in CU147 cells in the initial cultures inoculated with bird-propagated virus, but it grew rapidly after two passages in culture. In contrast, MSB1 (S) cells failed to become infected from the same bird-propagated virus used to infect CU147 cells, and even the virus from the $2^{nd}$ passage in CU147 cells grew to a lesser extent in MSB1 cells than in CU147 cells. The variance between the two studies was not due to a misidentification of the CIA-1 strain. Cross contamination was ruled out by sequencing the hypervariable region of Cux-1 and CIA-1 obtained from the titrations. The DNA sequence comparisons conducted with the two virus inocula and also with virus harvested from terminal dilutions of the titration of CIA-1 confirmed conclusively that the viruses were those intended. No other strains were being propagated in the laboratory at the time of these experiments. It is interesting to note that the comparative tests with PCR versus IF to detect infection were in general agreement although PCR detected a few terminal-dilution cultures missed by the IF test.

The standard substrate for growing CIAV in vitro has been the MSB1 cell line (von Bülow et al., "Chicken Infectious Anemia," *Diseases of Poultry*, $10^{th}$ ed., Iowa State University Press, pp. 739–756 (1997) and McNulty, "Chicken Anemia Agent," *A Laboratory Manual for the Isolation and Identification of Avian Pathogens*, $3^{rd}$ ed., Kendall/Hunt Publishing Co., Dubuque, Iowa, pp. 108–109 (1989), which are hereby incorporated by reference). The present invention demonstrates the usefulness and apparent superiority of CU147 as an alternate cell line for growing at least two strains of CIAV (Cux-1 and CIA-1) in vitro.

Although the invention has been described in detail for the purpose of illustration, it is understood that such detail is solely for that purpose, and variations can be made therein by those skilled in the art without departing from the spirit and scope of the invention which is defined by the following claims.

What is claimed:

1. A method of propagating chicken infectious anemia virus comprising:

providing a culture of Marek's disease chicken cell line—CU147 designated as ATCC Accession No. PTA-1476 and inoculating the culture with a chicken infectious anemia virus under conditions effective to propagate the virus in the culture.

2. The method according to claim 1, wherein the chicken infectious anemia virus is selected from the group consisting of CIA-1 strain, Cux-1 strain, Gifu strain, TK-5803 strain, CAA82-2 strain, L-028 strain, Conn strain, GA strain, 26P4 strain, SR43 strain, and CL-1 strain.

3. The method according to claim 1, wherein the culture of Marek's disease chicken cell line—CU147 designated as ATCC Accession No. PTA-1476 is established from early local lesions induced by Marek's disease virus and alloantigens.

4. The method according to claim 1, wherein said inoculating is at a rate from about 20 μL undiluted virus/ml culture to about 100 μL undiluted virus/ml culture.

* * * * *

SEQUENCE LISTING

```
<160> NUMBER OF SEQ ID NOS: 4

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence:  Primer O3F

<400> SEQUENCE: 1

caagtaattt caaatgaacg                                              20


<210> SEQ ID NO 2
```

-continued

```
<211> LENGTH: 20
<212> TYPE: DNA
<213> ORGANISM: Artificial Sequence
<220> FEATURE:
<223> OTHER INFORMATION: Description of Artificial Sequence: Primer O3R

<400> SEQUENCE: 2

ttgccatctt acagtcttat                                             20


<210> SEQ ID NO 3
<211> LENGTH: 19
<212> TYPE: DNA
<213> ORGANISM: Artificial Sequence
<220> FEATURE:
<223> OTHER INFORMATION: Description of Artificial Sequence: Primer O1F

<400> SEQUENCE: 3

aggtgtataa gactgtaag                                              19


<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: Primer
      PshA1R

<400> SEQUENCE: 4

gaacaggtgc cagcccccaa acat                                        24
```